United States Patent
Strommer et al.

(10) Patent No.: US 8,706,195 B2
(45) Date of Patent: Apr. 22, 2014

(54) METHOD FOR PRODUCING AN ELECTROPHYSIOLOGICAL MAP OF THE HEART

(75) Inventors: Gera Strommer, Haifa (IL); Uzi Eichler, Haifa (IL); Liat Schwartz, Haifa (IL); Arnit Cohen, Binyamina (IL)

(73) Assignee: MediGuide Ltd., Haifa (IL)

( * ) Notice: Subject to any disclaimer, the term of this patent is extended or adjusted under 35 U.S.C. 154(b) by 754 days.

(21) Appl. No.: 12/599,225

(22) PCT Filed: May 11, 2008

(86) PCT No.: PCT/IL2008/000656
§ 371 (c)(1),
(2), (4) Date: Sep. 30, 2010

(87) PCT Pub. No.: WO2008/136008
PCT Pub. Date: Nov. 13, 2008

(65) Prior Publication Data
US 2011/0021903 A1 Jan. 27, 2011

Related U.S. Application Data

(60) Provisional application No. 60/916,710, filed on May 8, 2007.

(51) Int. Cl.
*A61B 5/00* (2006.01)
(52) U.S. Cl.
USPC .......................................... 600/424; 600/425

(58) Field of Classification Search
None
See application file for complete search history.

(56) References Cited

U.S. PATENT DOCUMENTS

| | | | |
|---|---|---|---|
| 5,595,183 A | 1/1997 | Swanson et al. | |
| 5,878,336 A | 3/1999 | Cashen et al. | |
| 6,400,981 B1 | 6/2002 | Govari | |
| 6,690,963 B2 * | 2/2004 | Ben-Haim et al. | 600/424 |
| 6,716,166 B2 * | 4/2004 | Govari | 600/437 |
| 7,720,520 B2 * | 5/2010 | Willis | 600/424 |
| 8,180,428 B2 * | 5/2012 | Kaiser et al. | 600/411 |
| 8,190,238 B2 * | 5/2012 | Moll et al. | 600/424 |
| 2003/0018251 A1 * | 1/2003 | Solomon | 600/427 |
| 2003/0158477 A1 | 8/2003 | Panescu | |
| 2006/0084884 A1 * | 4/2006 | Beatty et al. | 600/523 |
| 2006/0095022 A1 * | 5/2006 | Moll et al. | 606/1 |

* cited by examiner

*Primary Examiner* — Unsu Jung
*Assistant Examiner* — Amanda Lauritzen Moher
(74) *Attorney, Agent, or Firm* — Dykema Gossett PLLC

(57) ABSTRACT

Method and system for producing an electrophysiological map of a heart of the body of a patient, the method including, for at least one target point, determining a respective target point location and a respective probe orientation, confirming that the tip of a probe is located at the respective target point location, confirming that the tip is oriented at the respective probe orientation, measuring at least one heart parameter value at the respective target point location, and superimposing at least one representation of the at least one heart parameter value on an image of the heart, at the respective target point location, to produce the electrophysiological map.

16 Claims, 15 Drawing Sheets

METHOD FOR PRODUCING AN ELECTROPHYSIOLOGICAL MAP OF THE HEART

CROSS-REFERENCE TO RELATED APPLICATONS

This application is a national stage filing based upon international application no. PCT/IL2008/000656, filed May 11, 2008 and published in English on Nov. 13, 2008 under international publication no. WO 2008/136008 (the '656 application), which claims priority to U.S. provisional application No. 60/916,710, filed May 8, 2007 (the '710 application). The '656 application and '710 application are both hereby incorporated by reference as though fully set forth herein.

FIELD OF THE DISCLOSED TECHNIQUE

The disclosed technique relates to medical devices in general, and to methods and systems for producing an electrophysiological map, in particular.

BACKGROUND OF THE DISCLOSED TECHNIQUE

Cardiac Arrhythmia is a well known medical condition where the regular beating rhythm of the heart is disrupted. These disruptions are caused by disturbances in the propagation path of electrical impulses in the myocardial tissue. These disturbances are caused, for example, by ischemia to a region in the myocardial tissue. Thus, the propagation of electrical impulses, through the myocardial tissue, may slow down. These ischemic regions create patterns of circular propagation of electric impulses. This circular propagation pattern disrupts the normal propagation pattern of electrical impulse, thus, causing irregular activation of the atria or ventricle. As a further example, cardiac arrhythmias are also caused by anatomical obstacles (e.g., dead tissue). These obstacles cause electric impulses to propagate around the obstacles, thus, disrupting the normal propagation of impulses to the atria or ventricular.

These conditions may be treated with an ablation procedure. During this procedure, a physician inserts an ablation catheter to the region of interest where abnormal propagation of electric impulses occurs, and ablates that region. This ablation is performed by using, for example, heat, electromagnetic pulses or cryogenic fluid.

Abnormal propagation pathways are found by an Electrophysiology Study procedure of the heart. During this procedure, a physician inserts into the heart, an electric potential measuring electrode or electrodes and stimulates the heart to create arrhythmia. During the arrhythmia, electric potential measuring electrodes measure the electric potential at different locations in the heart. Using this information, of a potential associated with a location, an electric potential map of the heart is formed. Consequently, the region of abnormal propagation of electric impulses can be located.

U.S. Patent Application Publication No. 2003/0158477 to Panescu and entitled "Systems and Methods for Guiding Catheters Using Registered Images", is directed to a system for producing a three-dimensional volume of the heart. The system includes a mapping catheter, a registration processor, a plurality of fiducials, and an external imaging device. The mapping catheter includes a plurality of mapping elements at a tip thereof. The fiducials are attached to the chest of the patient. The fiducials which show up on an image of the heart, can be used to register an externally acquired image with a three-dimensional coordinate system.

U.S. Pat. No. 5,595,183, to Swanson et al., entitled "Systems and Methods for Examining Heart Tissue Employing Multiple Electrode Structures and Roving Electrodes" (Swanson et al. '183),is directed to a system and a method for pacing and mapping the heart for the diagnosis and treatment of cardiac conditions. Swanson et al. '183 is direct to a system including a mapping probe and an ablation probe. The mapping probe carries a three dimensional multiple-electrode structure which takes the form of a basket. This basket structure is formed by splines extending from a base member (i.e., where the splines are connected to the catheter) to an end cap (i.e., where the splines are connected together). These splines are made from Nitinol metal or silicone rubber. A plurality of electrodes, are positioned on each of these splines. These electrodes are operative as either sensors or sources of electrical energy at the point of contact with the myocardial tissue.

The system to Swanson et al. operates in two modes, the sampling mode and the matching mode. In the sampling mode, the basket structure is deployed in the desired region of the heart. An electrode or pairs of electrodes are activated to produce electrical energy to the myocardial tissue, thus, pacing the heart. The electrodes then record electrograms. In the matching mode, the system compares the resulting paced electrogram morphologies, to a plurality of electrogram morphology templates collected during the sampling mode. Based upon this comparison, the system generates an output that identifies the location of an electrode or electrodes on the basket structure that are close to a possible ablation site. An ablation catheter is then inserted for ablating the site.

U.S. Pat. No. 5,876,336, to Swanson et al., entitled "Systems and Methods for Guiding Movable Electrode Elements Within Multiple-Electrode Structure" (Swanson et al. '336), is directed to a method and a system for remotely locating electrode elements at precise locations within the body of a patient. The system in Swanson et al. '336includes a mapping probe and an ablation probe. The mapping probe carries a three dimensional multiple-electrode structure which takes the form of a basket. This basket structure is formed by splines extending from a base member to an end cap. These splines are made from Nitinol metal or silicone rubber. A plurality of electrodes is positioned on each of these splines. These electrodes sense electrical activity in heart tissue. The sensed electrical activity is processed to create a map of this electrical activity. A physician uses this map to identify regions for possible ablation.

Once a region is selected for ablation, an ablation probe (i.e., ablation catheter), including an ablation electrode, is inserted to the heart and placed in contact with the tissue in the selected region. The ablation electrode emits ablation energy (e.g., heat or electromagnetic energy) to the contacted heart tissue, to destroy that tissue.

The system to Swanson et al. includes a processing unit for guiding the ablation catheter. This processing unit determines the position of the ablation catheter within the space defined by the basket structure in terms of the relative position of the electrodes deposited on the splines of the basket. The position information of the ablation catheter aids a physician in guiding the ablation catheter. This position information is further displayed to the physician.

According to Swanson et al. '336, the position of the ablation catheter within the basket structure is determined using the electrodes deposited on the splines. First, the position of the ablation catheter in a horizontal sector, between adjacent horizontal sets of electrodes, is determined. This horizontal sector is determined by sensing the phase difference between the phase of an oscillator signal, sequentially applied to each set of electrodes, and the phase of the ablation electrode. If the ablation catheter is beneath the electrode set, the phase difference sign is negative. If the ablation catheter is above the electrode set, the phase difference sign is positive. Next, an arcuate sector symmetrically bisected by a spline is determined.

This arcuate sector is determined using differential amplitude sensing or differential phase sensing between the ablation electrode and a spline, to which an oscillating signal is applied. The arcuate sector, bisected by the spline yielding the smallest amplitude difference or the smallest phase difference, is selected. The bisection of the horizontal sector with the arcuate sector forms a pie shaped sector. The position of the ablation catheter in the pie shaped sector is determined according to the distance of the ablation catheter from the basket electrodes. The closer the ablation catheter is to the electrodes, the higher the peak voltage sensed from these electrodes. Thus, the distance from the electrodes is determined according to the sensed peak voltage during the determination of the arcuate sector.

U.S. Pat. No. 6,400,981, to Govari, entitled "Rapid Mapping of Electrical Activity in the Heart," is directed to a method for mapping electrical potentials inside a volume. In Govari, a mapping catheter including a plurality of electrodes is inserted into a chamber of the heart, to generate a map of the electrical activity over an endocardial surface of the heart. These electrodes are distributed over the surface of the distal part of the catheter. The catheter further includes at least one position sensor at the distal part of the catheter. A geometrical model of the endocardial surface is formed by the catheter. Electrical potentials are measured within the volume of the chamber using the electrodes on the catheter. Since the position of the electrodes with respect to the position sensor is known, the measured potentials are combined with the geometrical model, thus generating a map of the electrical potentials at the endocardial surface.

SUMMARY OF THE DISCLOSED TECHNIQUE

It is an object of the disclosed technique to provide a novel method and system for producing an electophysiological map of a heart of the body of a patient. In accordance with the disclosed technique, there is thus provided a method for producing an electrophysiological map of a heart of the body of a patient. The method includes the procedures of determining a respective target point location, and a respective probe orientation, confirming that the tip of a probe catheter is located at the respective target point location, and confirming that the tip is oriented at the respective probe orientation. The method further includes the procedures of measuring the heart parameter value at each of the respective target point locations, and superimposing a plurality of representations respective of the heart parameter value.

The target point location, and probe orientation, are determined with respect to a heart parameter value, which is to be measured, for each of a plurality of target points within the heart. It is confirmed that the tip of a probe catheter is located at the respective target point location, by comparing the currently detected location of the tip, with the respective target point location. It is confirmed that the tip is oriented at the respective probe orientation, by comparing the currently detected orientation of the tip, with the respective probe orientation. The heart parameter value at each of the respective target point locations, is measured by a heart parameter sensor located at the tip. The representations respective of the heart parameter value, are superimposed on an image of the heart, at the respective target point location, to produce the electrophysiological map.

In accordance with another aspect of the disclosed technique, there is thus provided a method for producing an electrophysiological map of the heart. The method includes the procedures of registering a medical positioning system (MPS) with an image detector, navigating a probe catheter to a plurality of points within a heart chamber of the heart, and detecting a heart parameter at each of the points. The method further includes the procedures of determining the position at each of the points, associating each of the heart parameters with a respective one of the positions, and constructing an electrophysiological map of the heart chamber, according to a plurality of pairs of the heart parameters and the respective positions.

The MPS is registered with an image detector, wherein the image detector detects the image of the heart. The probe catheter is navigated to a plurality of points within the heart chamber, according to a representation of the position of an electrophysiological probe located at the tip of the probe catheter, in the image. The probe catheter includes an MPS sensor in the vicinity of the electrophysiological probe. The MPS sensor is coupled with the MPS. The MPS sensor detects the position. The heart parameter is detected at each of the points, by the electrophysiological probe. The position at each of the points, is determined according to an output of the MPS sensor. An electrophysiological map of the heart chamber is constructed, according to a plurality of pairs of the heart parameters and the respective positions.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by marking a plurality of strategic points on an image of the heart, and measuring the electric potential of the heart at each one of these points, by employing a probe catheter, after confirming that the tip of the probe catheter is located at each point, at a suitable orientation, relative to the surface of the tissue of the heart. A medical positioning system (MPS), and an MPS sensor located at the tip of the probe catheter, can be employed for determining the location and orientation of the tip of the catheter. Since an MPS coordinate system of the MPS is registered with an image coordinate system of the image of the heart (either three-dimensional or two-dimensional), a processor can superimpose a representation of the value of each of the electric potential measurements, on the strategic points on the image of the heart, to produce an electrophysiological map.

Additionally, a potentiometer can be coupled with the probe catheter, to measure a change in electric potential at each point, due to a stimulated pulse at the coronary sinus of the heart, and measuring the local activation time (LAT). In this manner, an LAT map of the heart can be constructed. Further additionally, an electrocardiogram (ECG) can be employed for compensating for the movements of the heart, during contractions. In this manner, a still image of the heart can be displayed, in order to facilitate marking the points on the image of the heart, despite the movements of the heart.

The term "heart parameter" herein below, refers to a parameter specific to the heart, which can be measured by a probe, such as electric potential, LAT, and the like. The term "tomographic image detector" herein below, refers to an image detector which acquires a plurality of 2D images from different sections of an organ of a patient. The tomographic image detector can be a computed tomography (CT), magnetic resonance imager (MRI), positron emission tomography (PET), single photon emission computer tomography (SPECT), ultrasound image detector, infrared image detector, X-ray imager, and the like. The tomographic image detector can produce a 3D image of the organ, by reconstructing the 2D images. The tomographic image detector can acquire the images either prior to the operation (i.e., preoperative image detector), such as CT, MRI, PET, SPECT, or in real-time (i.e., real-time image detector), as in the case of ultrasound, infrared and X-ray.

The term "2D image detector" herein below, refers to an image detector which acquires a two-dimensional image of the organ, such as fluoroscope, ultrasound, and the like. In the description herein below, the term "image detector" interchangeably refers to a tomographic image detector, as well as a 2D image detector. The term "position" herein below, refers either to the location, to the orientation or both the location and the orientation, of an object in a three-dimensional coordinate system.

Figure 1A:
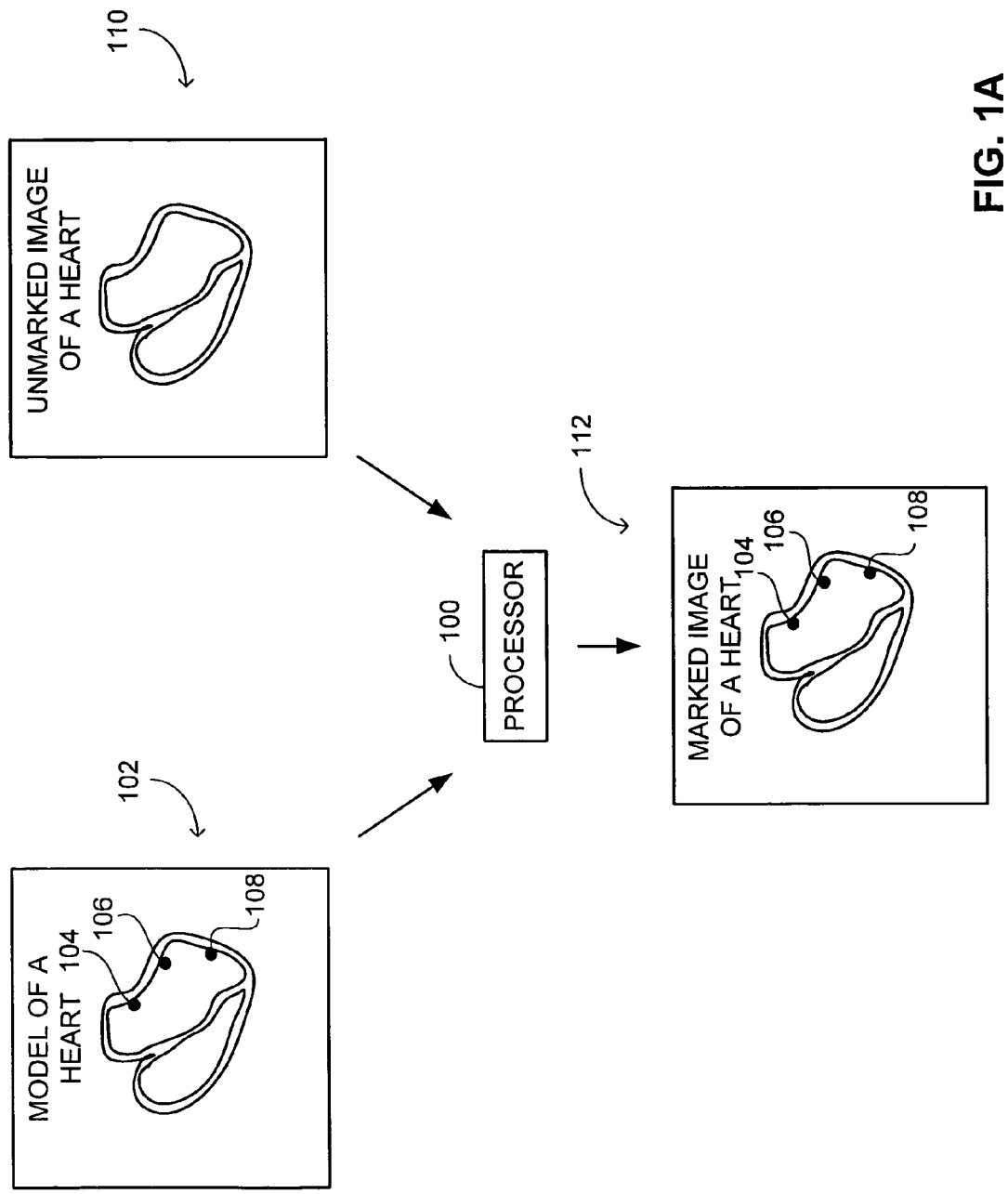
FIG. 1A is a schematic illustration of a marked image of a heart of the body of a patient, produced according to an embodiment of the disclosed technique.
Figure 1B:
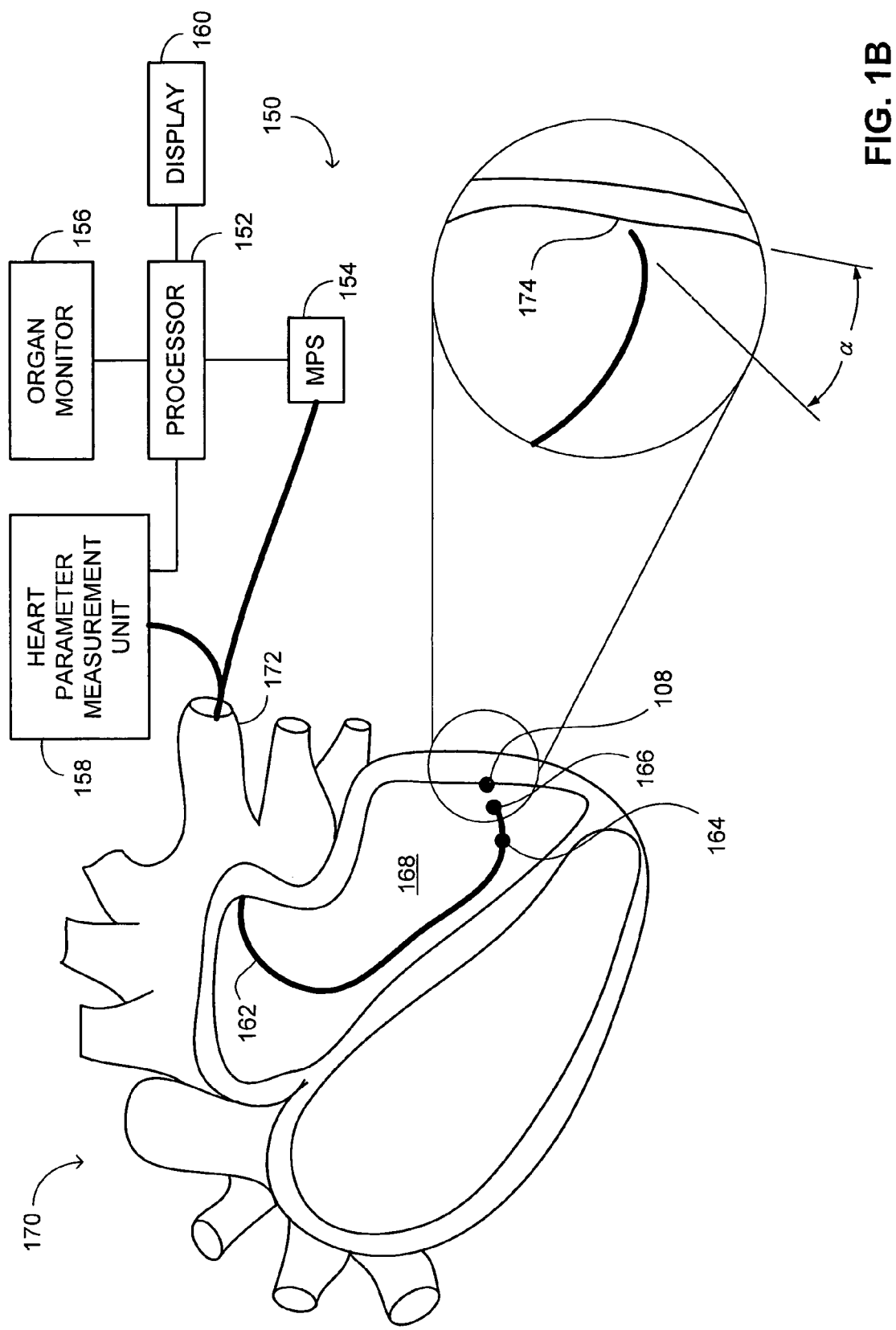
FIG. 1B is a schematic illustration of a system for measuring a heart parameter after confirming that the tip of a probe catheter is located at a target point in the marked image of FIG. 1A, and oriented at a predetermined orientation, constructed and operative according to another embodiment of the disclosed technique.

Reference is now made to FIGS. 1A, and 1B. FIG. 1A is a schematic illustration of a marked image of a heart of the body of a patient, generally referenced 112, produced according to an embodiment of the disclosed technique. FIG. 1B is a schematic illustration of a system generally referenced 150, for measuring a heart parameter after confirming that the tip of a probe catheter is located at a target point in the marked image of FIG. 1A, and oriented at a predetermined orientation, constructed and operative according to a further embodiment of the disclosed technique.

With reference to FIG. 1A, a processor 100 includes data respective of a model 102 of a representative heart (not shown). Model 102 includes data respective of the location of a plurality of target points 104, 106, and 108, within the representative heart. Each of target points 104, 106, and 108, is defined as a point within a typical heart, at which an electrophysiological parameter is to be measured. An image detector (not shown), acquires an unmarked image 110 of a heart (not shown) of a body (not shown) of a patient (not shown). Processor 100 registers unmarked image 110 with model 102, and produces marked image 112, by superimposing target points 104, 106, and 108, on unmarked image 110. Alternatively, a surgeon (not shown) can direct processor 100 to produce marked image 112, by manually marking target points 104, 106, and 108 on unmarked image 110, via a user interface (not shown), for example, based on the symptoms of the patient, a previous diagnosis of the patient, and the like.

With reference to FIG. 1B, system 150 includes a processor 152, an MPS 154, an organ monitor 156, a heart parameter measurement unit 158, a display 160, and a probe catheter 162. Probe catheter 162 includes an MPS sensor 164, and a heart parameter sensor 166, at a tip thereof. Processor 152 is coupled with MPS 154, organ monitor 156, heart parameter measurement unit 158, and with display 160. MPS sensor 164 is coupled with MPS 154. Heart parameter sensor 166 is coupled with heart parameter measurement unit 158.

Organ monitor 156 is a device which detects an organ timing signal of an organ (not shown), of the body of the patient, such as the ECG of the heart, a respiration signal of the lungs (not shown), of the body of the patient, and the like. MPS 154 is a device which determines the position of MPS sensor 164 (i.e., the position of the tip of probe catheter 162), according to an output of MPS sensor 164, which MPS sensor 164 produces in response to an electromagnetic field. It is noted that instead of MPS 154 other position detectors known in the art, such as sonar, optical, and the like, can be employed.

Processor 152 directs display 160 to display marked image 112 (FIG. 1A). Marked image 112 is a previously acquired image of a heart 170 of the body of the patient, on which a plurality of target points, such as target point 108, are superimposed. Processor 152 can direct display 160 to display marked image 112, according to a real-time organ timing signal of heart 170. Hence, it is not necessary to expose the patient and a surgeon (not shown) to the ionizing radiation (e.g., X-rays) of the image detector, while performing the medical operation on the patient. The surgeon enters probe catheter 162 into a left ventricle 168 of heart 170, through a pulmonary vein 172. MPS 154 determines the current position of the tip of probe catheter 162, according to an output of MPS sensor 164. Processor 152 produces a superimposed image (not shown) of heart 170, by superimposing a representation of the position of the tip of probe catheter 162, on marked image 112. Hence, the surgeon is able to observe a real-time representation of the tip of probe catheter 162, as the surgeon navigates probe catheter 162 within left ventricle 168.

Before directing heart parameter measurement unit 158 to measure a heart parameter, it has to be confirmed that the tip of probe catheter 162 is located at target point 108 (i.e., target point location), and that furthermore, the tip of probe catheter 162 is oriented at a predetermined orientation relative to a surface 174 of left ventricle 168 (e.g., an angle α). It is noted that for heart parameter sensor 166 to detect a reliable value of the heart parameter, the value of angle α has to be within a predetermined range of angles. This is due to the fact that a reading of heart parameter sensor 166 depends on the orientation of heart parameter sensor 166, at point of contact with the tissue of left ventricle 168.

The surgeon can visually confirm the location of the tip of probe catheter 162, by observing an image (not shown) of a radiopaque marker (not shown), located at the tip of probe catheter 162, on a real-time image (not shown) of heart 170 (e.g., a fluoroscope). Alternatively, the surgeon can confirm the location of the tip of probe catheter 162, by observing the representation of the tip of probe catheter 162, which processor 152 produces according to an output of MPS 154. On the other hand, the orientation of the tip of probe catheter 162 can be confirmed only according to the output of MPS 154. Further alternatively, instead of the confirmation by the surgeon, the processor can direct a user interface (not shown) coupled therewith, to notify the surgeon that the tip of the probe catheter is located at the target point, and is oriented at the predetermined orientation, for example, by producing an aural or visual output, and the like. Alternatively, instead of a manual navigation by the surgeon, an automatic navigation system coupled with the processor, can be employed for automatically maneuvering and navigating the probe catheter within the body of the patient, and within the left ventricle, according to a previously acquired topological map of the circulation system of the body of the patient.

After confirming the location and orientation of the tip of probe catheter 162, processor 152 directs heart parameter measurement unit 158 to measure the heart parameter at target point 108, according to the output of heart parameter sensor 166. Heart parameter measurement unit 158 measures the heart parameter at additional target points such as target points 104 and 106 (FIG. 1A). Processor 152 produces an electrophysiological map (not shown) of heart 170, for example, by interpolating between the individual heart parameter values, and directs display 160 to display this electrophysiological map.

Figure 2:
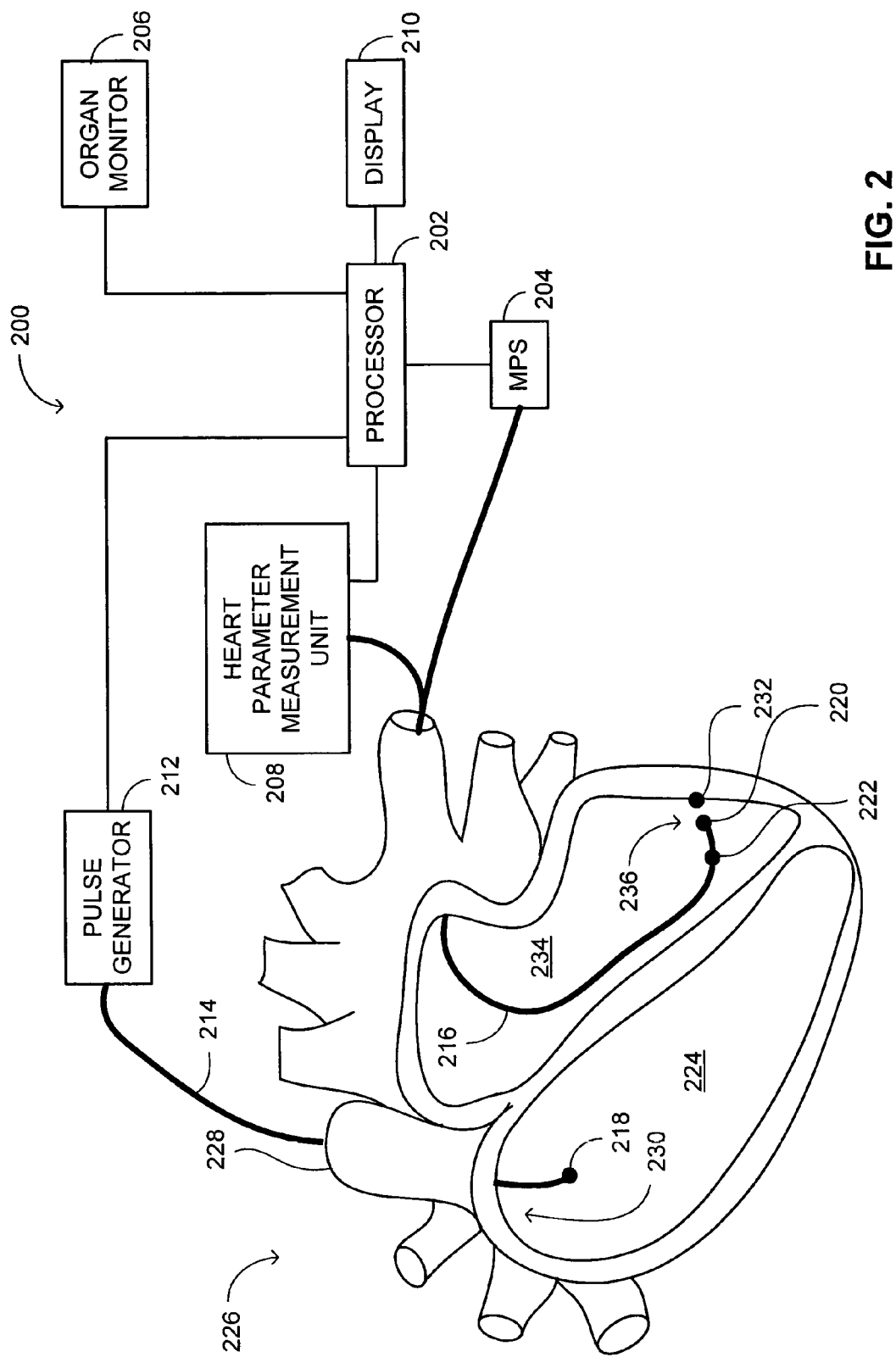
FIG. 2 is a schematic illustration of a system for measuring a heart parameter of a heart of the body of a patient, constructed and operative according to a further embodiment of the disclosed technique.

Reference is now made to FIG. 2, which is a schematic illustration of a system generally referenced 200, for measuring a heart parameter of a heart of the body of a patient, constructed and operative according to a further embodiment of the disclosed technique. System 200 includes a processor 202, an MPS 204, an organ monitor 206, a heart parameter measurement unit 208, a display 210, a pulse generator 212, a stimulation catheter 214, and a probe catheter 216. Stimulation catheter 214 includes an electrode 218 at the tip thereof. Probe catheter 216 includes a heart parameter sensor 220 and an MPS sensor 222, at the tip thereof.

Processor 202 is coupled with MPS 204, organ monitor 206, heart parameter measurement unit 208, display 210, and with pulse generator 212. Electrode 218 is coupled with pulse generator 212. Heart parameter sensor 220 is coupled with heart parameter measurement unit 208. MPS sensor 222 is coupled with MPS 204.

The surgeon enters stimulation catheter 214 into a right ventricle 224 of a heart 226 of the body of a patient (not shown), through a superior vena cava 228 of heart 226, and maintains electrode 218 at a sinoatrial node 230 of heart 226. The surgeon positions the tip of probe catheter 216 at a target point 232 in a left ventricle 234 of heart 226, as described herein above in connection with FIGS. 1A and 1B.

Processor 202 directs pulse generator 212 to produce an electric pulse at electrode 218. This electric pulse travels within right ventricle 224 and left ventricle 234, substantially similar to the way a pulse produced by sinoatrial node 230, would travel within right ventricle 224 and left ventricle 234. Heart parameter sensor 220 constantly senses the electric potential at target point 232. Once the electric pulse produced by electrode 218 reaches a region 236 of left ventricle 234, heart parameter sensor 220 senses an electric potential differential and produces an output, accordingly. Heart parameter measurement unit 208 determines the value of this electric potential differential, according to the output of heart parameter sensor 220.

Processor 202 determines the time interval (i.e., local activation time—LAT) between the moment pulse generator 212 produces the electric pulse, and the moment heart parameter sensor 220 senses the electric potential differential. Processor 202 determines additional values of LAT at other target points within heart 226, while electrode 208 is maintained at sinoatrial node 230, and probe catheter 216 is moved to other target points within heart 226. Processor 202 produces an LAT map of heart 226, similar to the way system 150 (FIG. 1B) produces an electrophysiological map of heart 170, as described herein above. Processor 202 directs display 210 to display this LAT map of heart 226.

Figure 3:
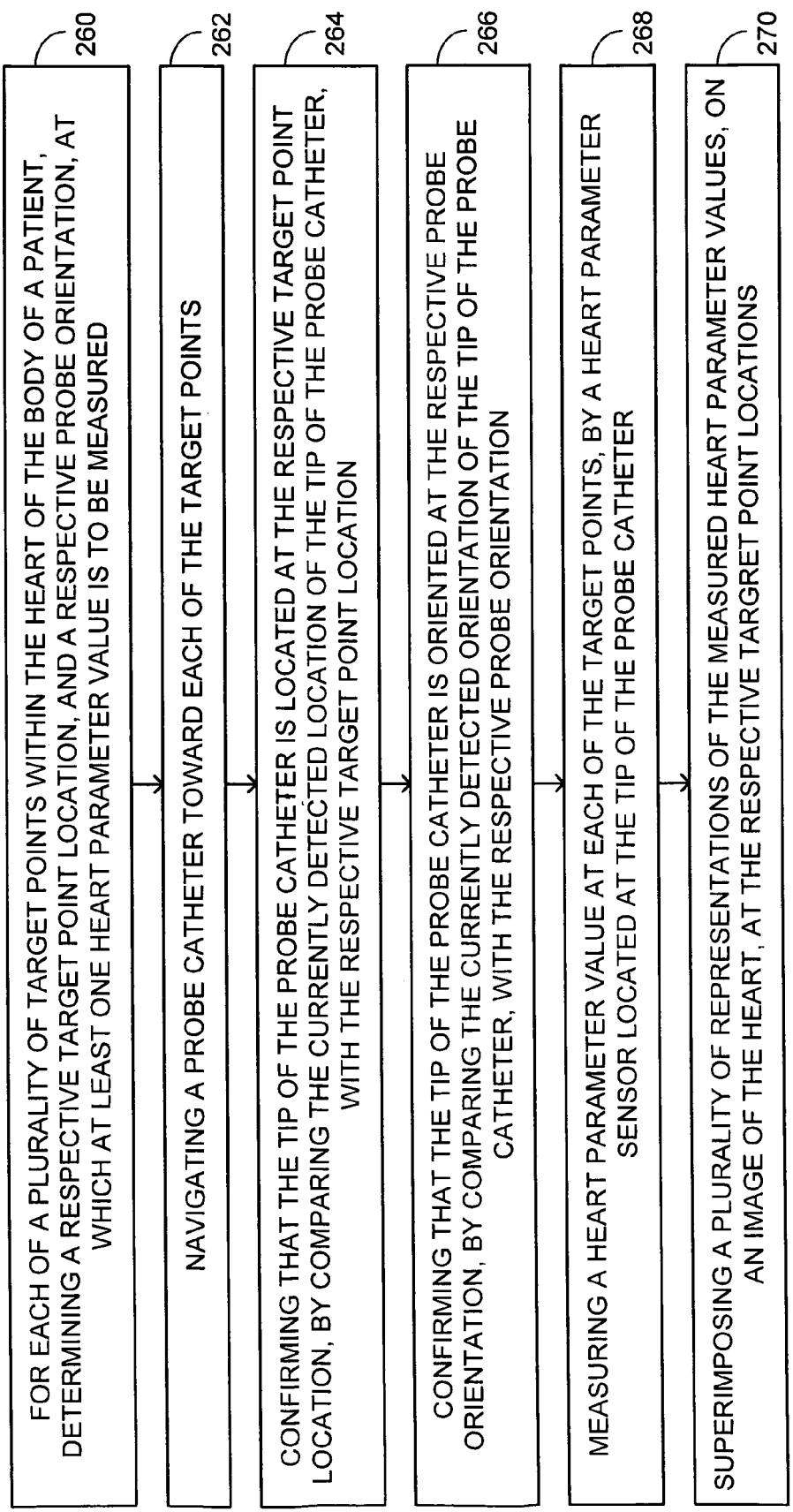
FIG. 3 is a schematic illustration of a method for operating the systems of FIGS. 1A, 1B, and 2, operating according to another embodiment of the disclosed technique.

Reference is now made to FIG. 3, which is a schematic illustration of a method for operating the systems of FIGS. 1A, 1B, and 2, operating according to another embodiment of the disclosed technique. In procedure 260, for each of a plurality of target points within the heart of the body of a patient, a respective target point location, and a respective probe orientation are determined, at which at least one heart parameter value is to be determined. With reference to FIG. 1A, processor 100 produces marked image 112 of the heart of the patient, in which target points 104, 106, and 108 are marked (i.e., processor 100 determines a plurality of target point locations). Processor 100, additionally, determines a range of orientations for the tip of probe catheter 162 (FIG. 1B), which probe catheter 162 has to assume, before sensing the respective heart parameter.

In procedure 262, a probe catheter is navigated toward each of the target points. In this procedure, the surgeon navigates probe catheter 162 to target point 108. Alternatively, an automatic navigation system can be employed for automatically navigating probe catheter 162 to target point 108.

In procedure 264, it is confirmed that the tip of the probe catheter is located at the respective target point location, by comparing the currently detected location of the tip of the probe catheter, with the respective target point location. With reference to FIG. 1B, processor 152 compares the current location of the tip of probe catheter 162, according to an output of MPS 154, with the target point location of target point 108, according to marked image 112 (FIG. 1A), and determines whether the current location substantially matches the target point location.

In procedure 266, it is confirmed that the tip of the probe catheter is oriented at the respective probe orientation, by comparing the currently detected orientation of the tip of the probe catheter, with the respective probe orientation. With reference to FIG. 1B, processor 152 compares the current probe orientation of the tip of probe catheter 162, according to the output of MPS 154, with the range of orientations for the tip of probe catheter 162, as determined in procedure 260, and determines whether the current probe orientation substantially matches the range of orientations.

In procedure 268, a heart parameter value is measured at each of the target points, by a heart parameter sensor located at the tip of the probe catheter. With reference to FIG. 1B, heart parameter measurement unit 158 measures the heart parameter at target point 108, according to the output of heart sensor 166.

In procedure 270, a plurality of representations of the measured heart parameter values, are superimposed on an image of the heart, at the respective target point locations. With reference to FIG. 1B, processor 152 determines additional heart parameter values at other target points, between target points 104, 106, and 108, and superimposes a plurality of representations respective of these heart parameter values, on an image of heart 170, thereby producing an electrophysiological map of heart 170.

According to another aspect of the disclosed technique, the surgeon navigates a probe catheter to a plurality of known points within a heart chamber (i.e., also known as the cardiac chamber) of the heart of the patient, by visually observing the heart parameter sensor of the probe catheter and a representation of the position of the sensor, at these known points, in respective images of the heart chamber. The probe catheter includes an MPS sensor close to the heart parameter sensor. The MPS, which is coupled with the MPS sensor, is registered with the coordinate system of the image detector, which detects a three dimensional image of the heart chamber. Therefore, the processor can determine the position of the heart parameter sensor at each of these points, and associate it with the respective heart parameter, as detected by the sensor. In this manner, the processor can construct an electrophysiological map of the heart chamber. The three dimensional image can, for example, be a computerized tomography generated image, which defines the inner surface of the cardiac heart chamber. The surgeon maneuvers the probe to known points on that inner surface, the MPS sensor confirms arrival at these known points and the heart parameter sensor measures a desired parameter (e.g., electric potential, temperature, pressure) at each of these points. After gathering enough information, the processor can generate a map of this parameter on the inner surface.

Figure 4A:
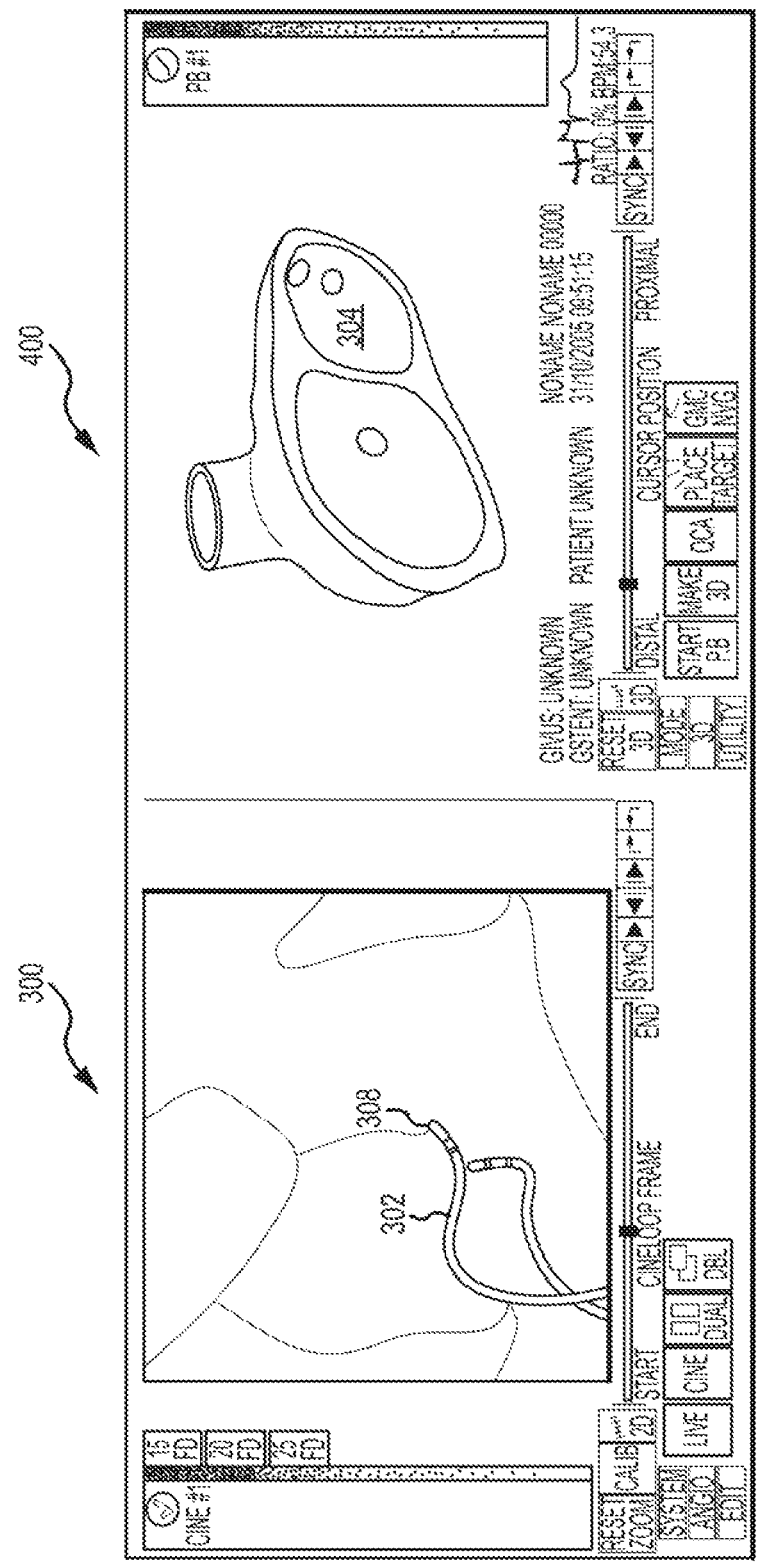
FIG. 4A is a schematic illustration of a graphical user interface (GUI) including a real-time two-dimensional image of the heart chamber of the heart of the body of a patient, and a previously acquired three-dimensional image of the heart chamber, at a stage prior to registration of an MPS with an image detector detecting the two-dimensional image, constructed and operative according to a further embodiment of the disclosed technique.
Figure 4B:
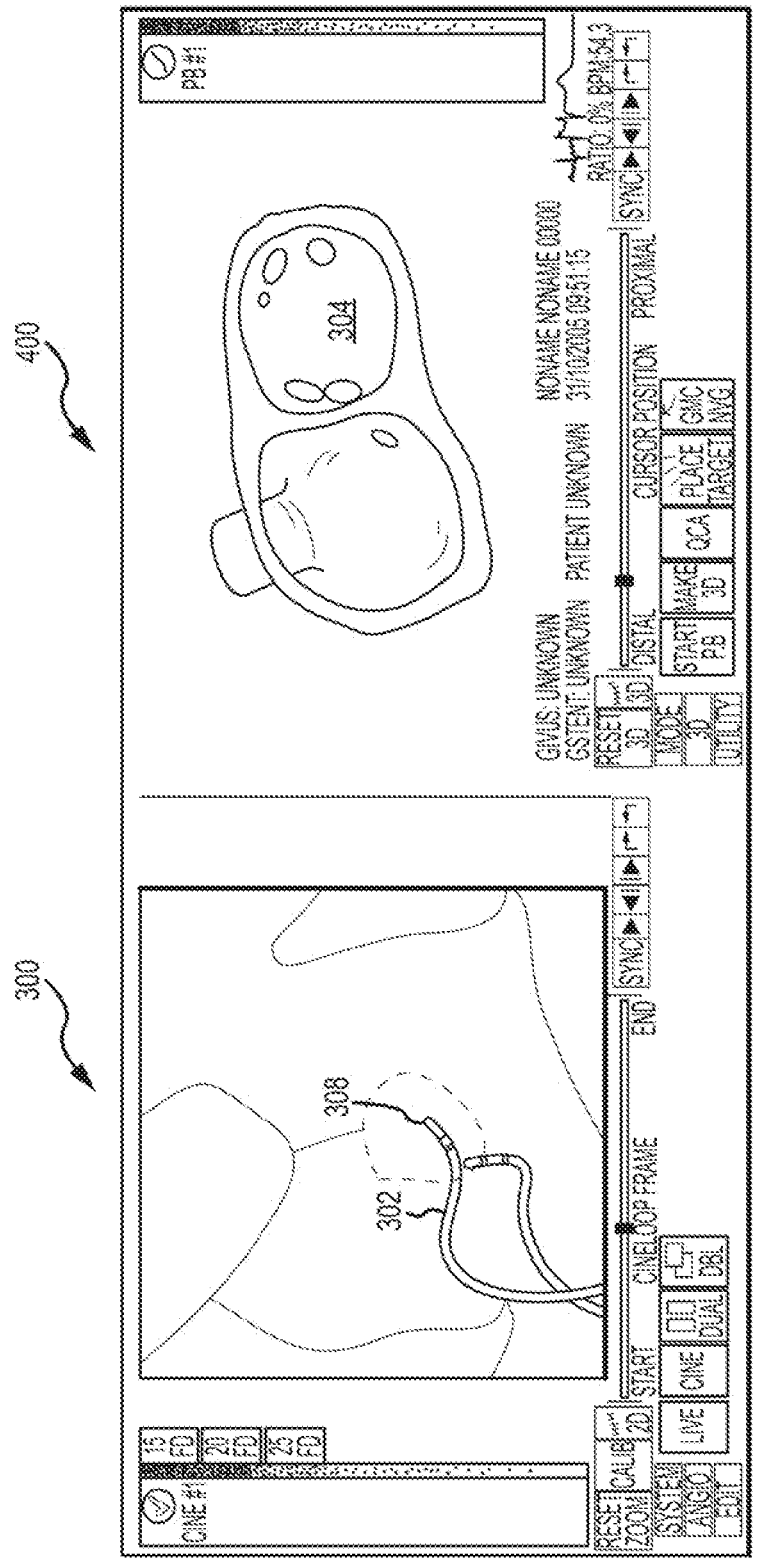
FIG. 4B is a schematic illustration of the GUI of FIG. 4A, during registration of the MPS with the image detector.
Figure 4C:
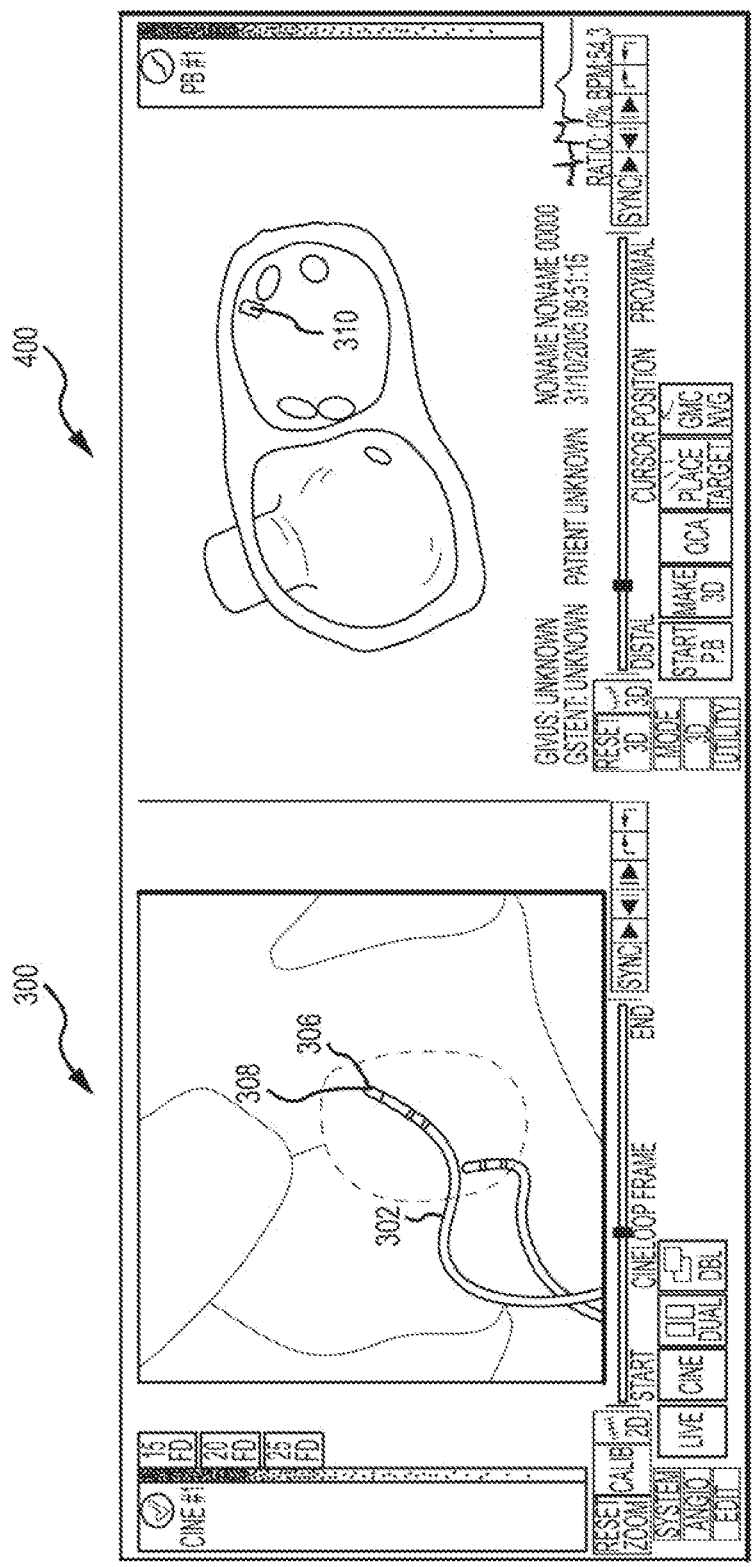
FIG. 4C is a schematic illustration of the GUI of FIG. 4A, during navigation of a probe catheter within the heart chamber.
Figure 4D:
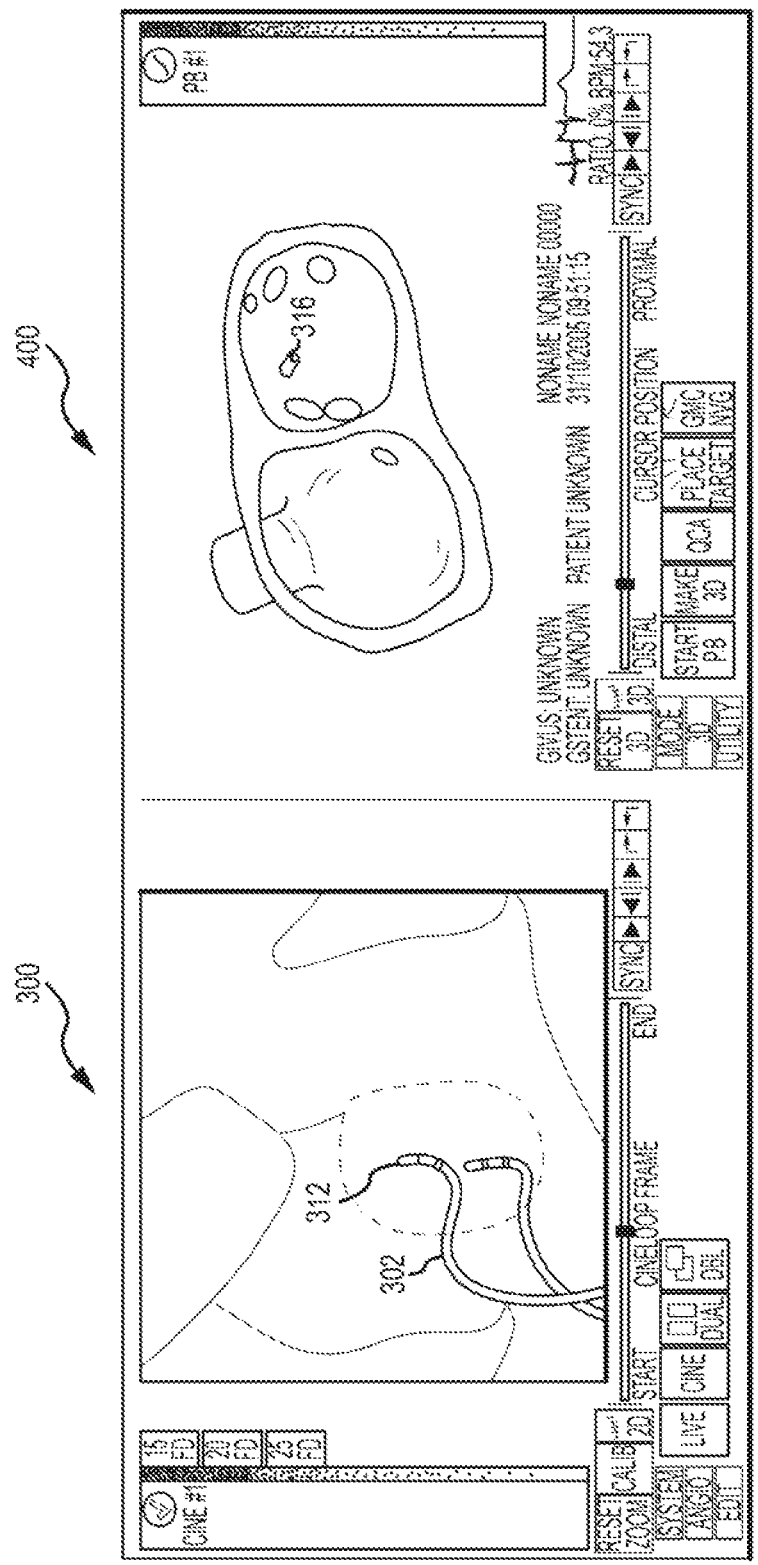
FIG. 4D is a schematic illustration of the GUI of FIG. 4C, during further navigation of the probe catheter of FIG. 4C, to another point within the heart chamber.
Figure 4E:
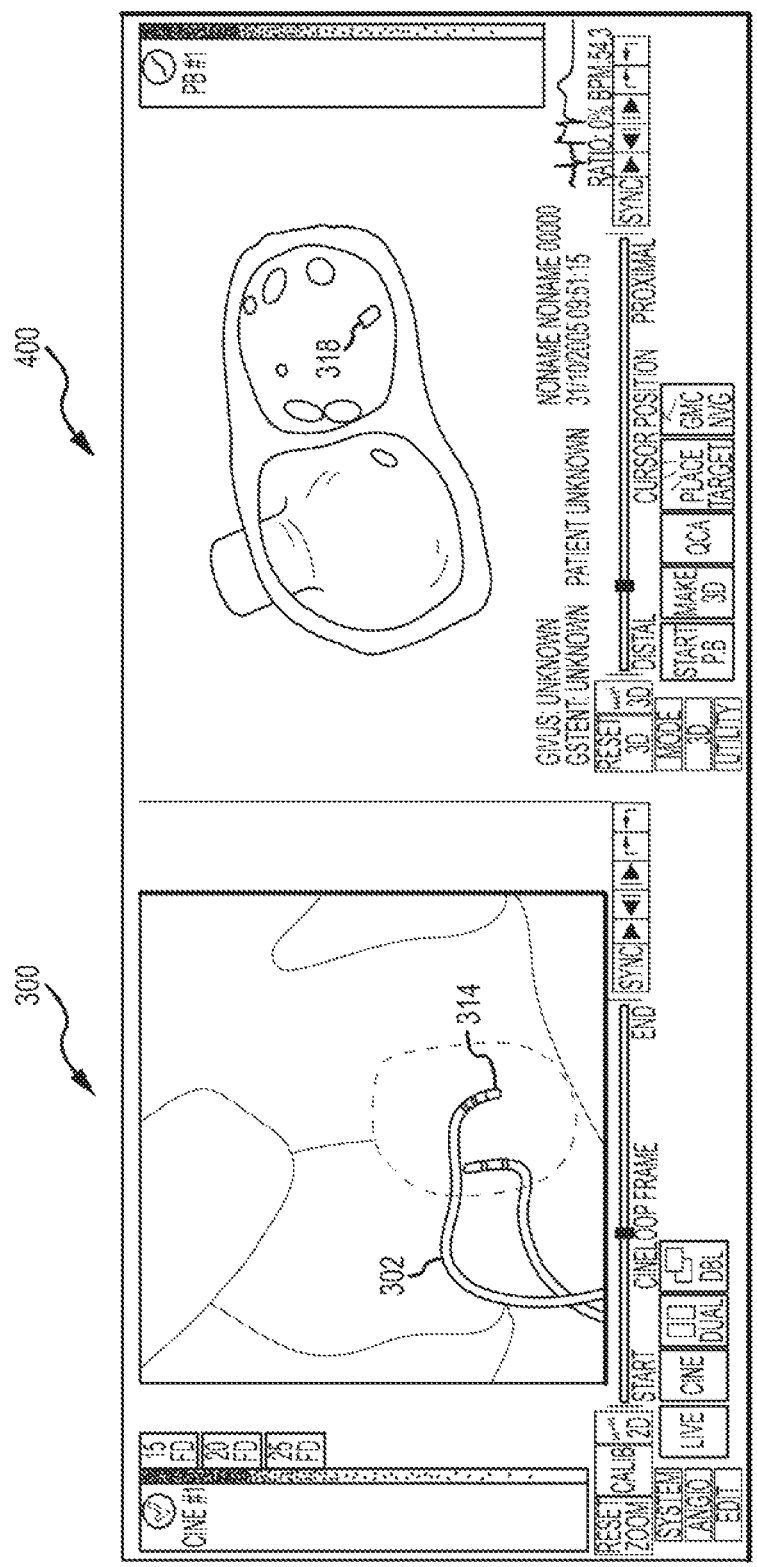
FIG. 4E is a schematic illustration of the GUI of FIG. 4C, during navigation of the probe of FIG. 4C, to a further point within the heart chamber.
Figure 4F:
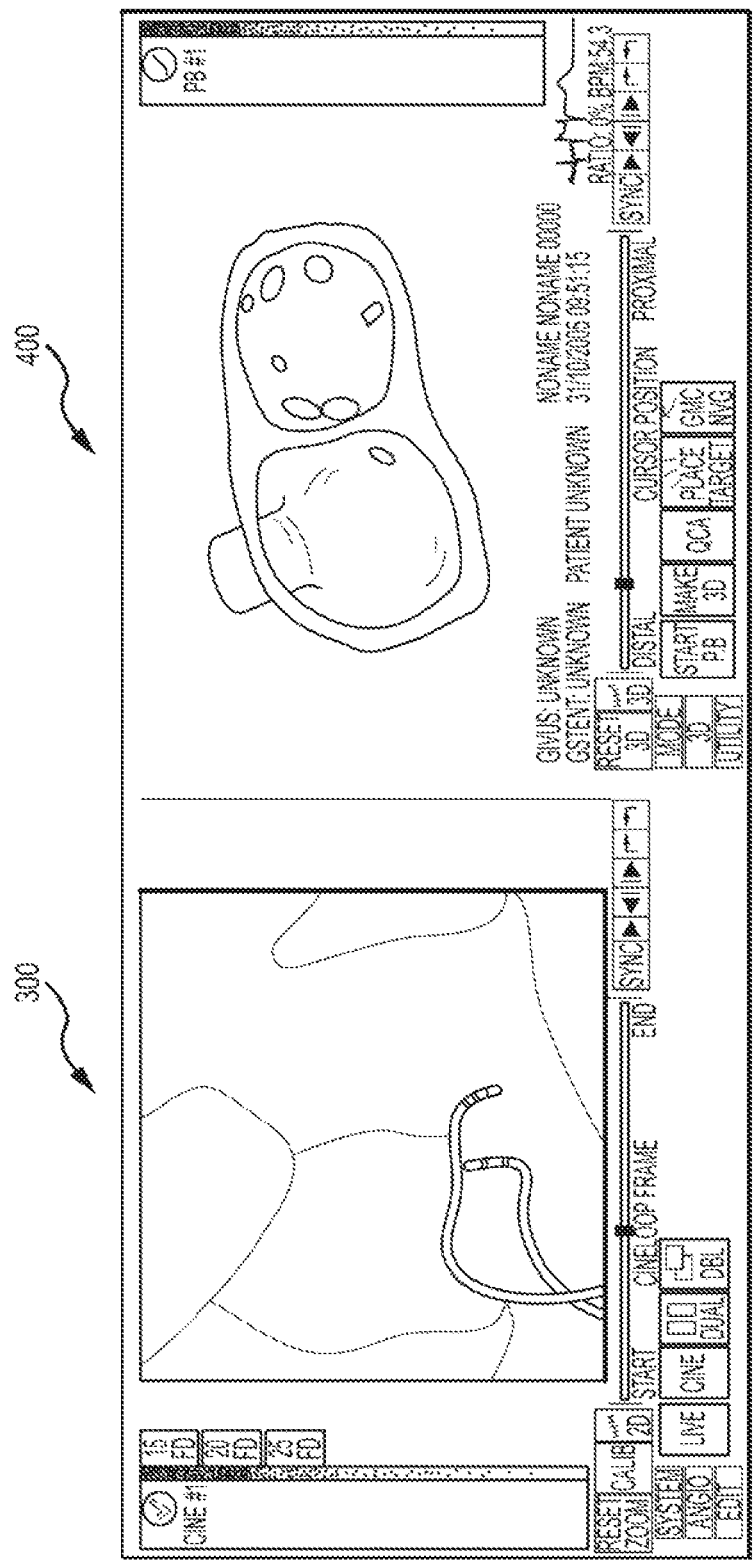
FIG. 4F is a schematic illustration of the GUI including a two-dimensional real-time image of the heart chamber, and a previously acquired three-dimensional image of the heart chamber, including an electrophysiological map the heart chamber, constructed and operative according to a further embodiment of the disclosed technique.
Figure 4G:
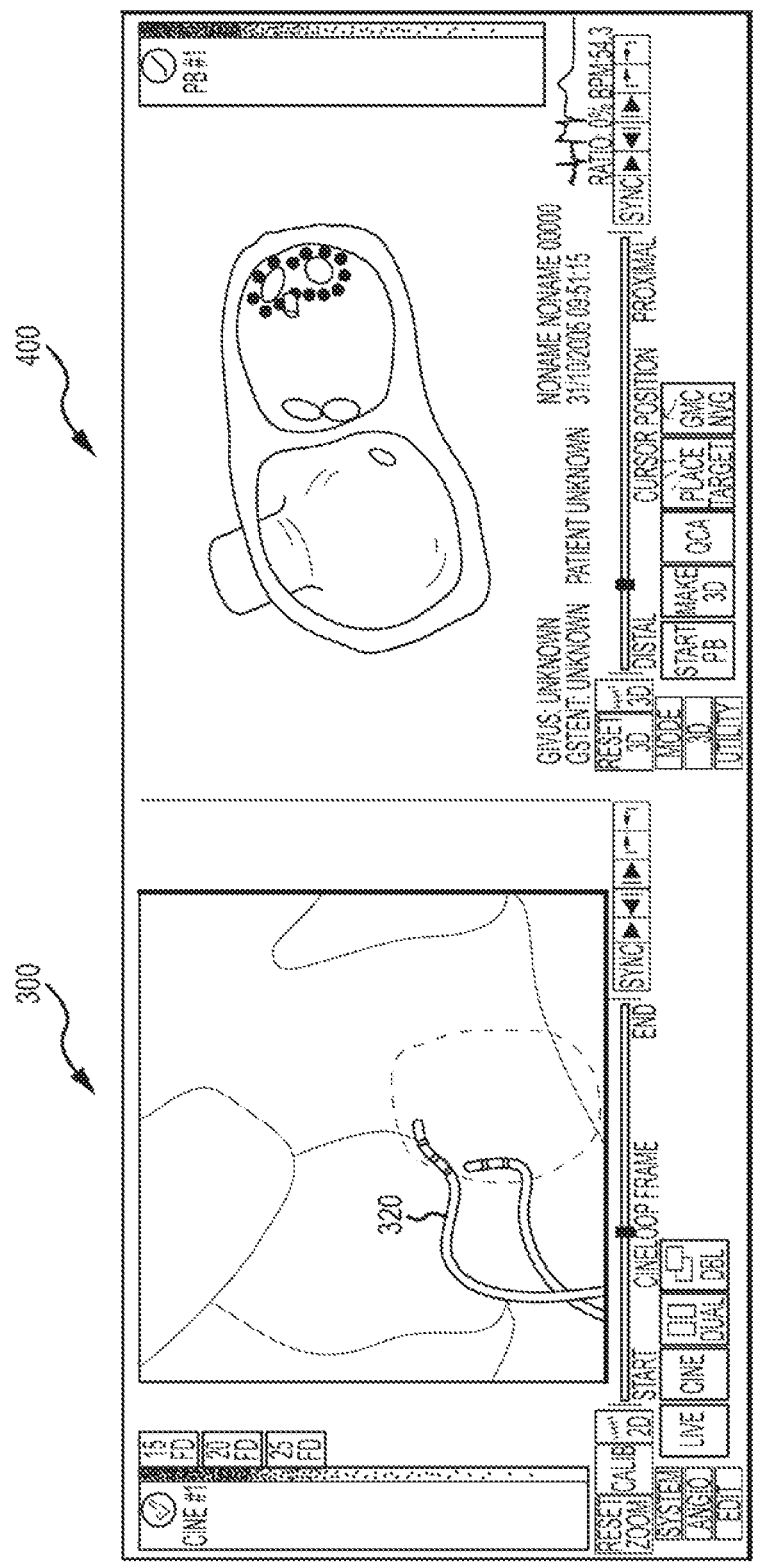
FIG. 4G is a schematic illustration of the GUI of FIG. 4F, during ablation of a region of a pulmonary vein of the heart of the patient.
Figure 4H:
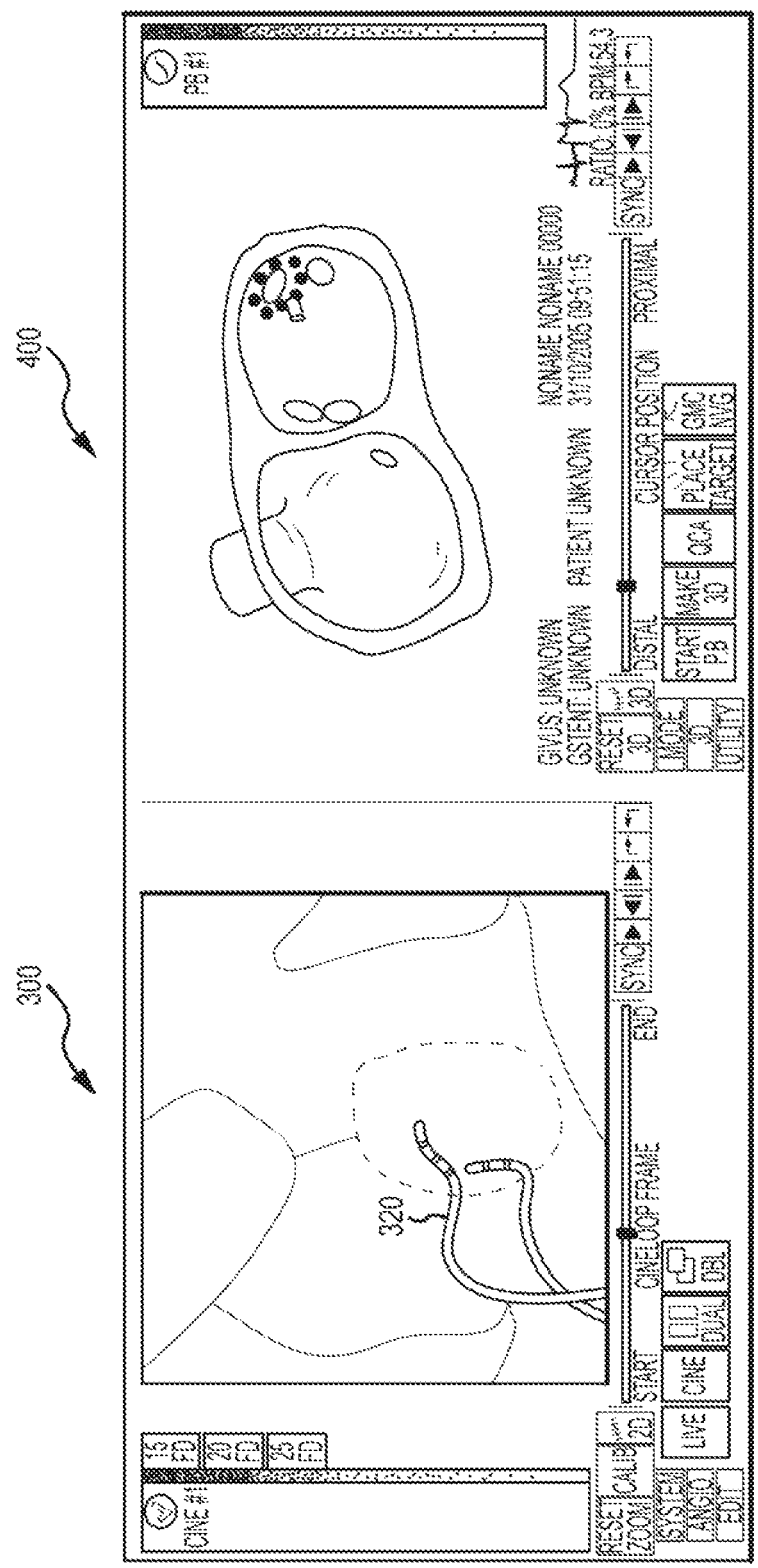
FIG. 4H is a schematic illustration of the GUI of FIG. 4F, during ablation of another region of the pulmonary vein of the heart.
Figure 4J:
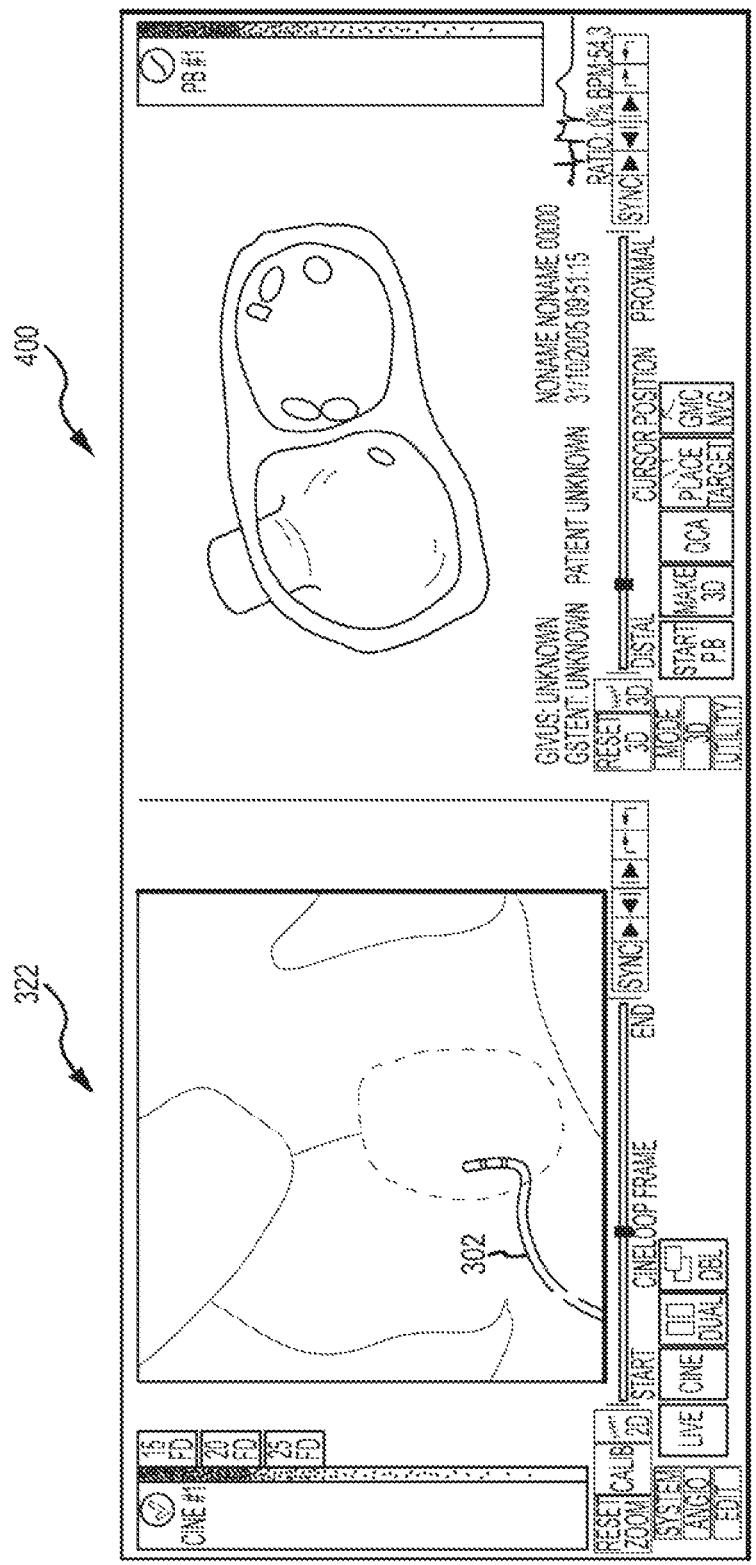
FIG. 4J is a schematic illustration of a GUI including a previously acquired two-dimensional image of the heart chamber, and a previously acquired three-dimensional image of the heart chamber, constructed and operative according to another embodiment of the disclosed technique, during navigation of the probe catheter to a point within the heart chamber.
Figure 4K:
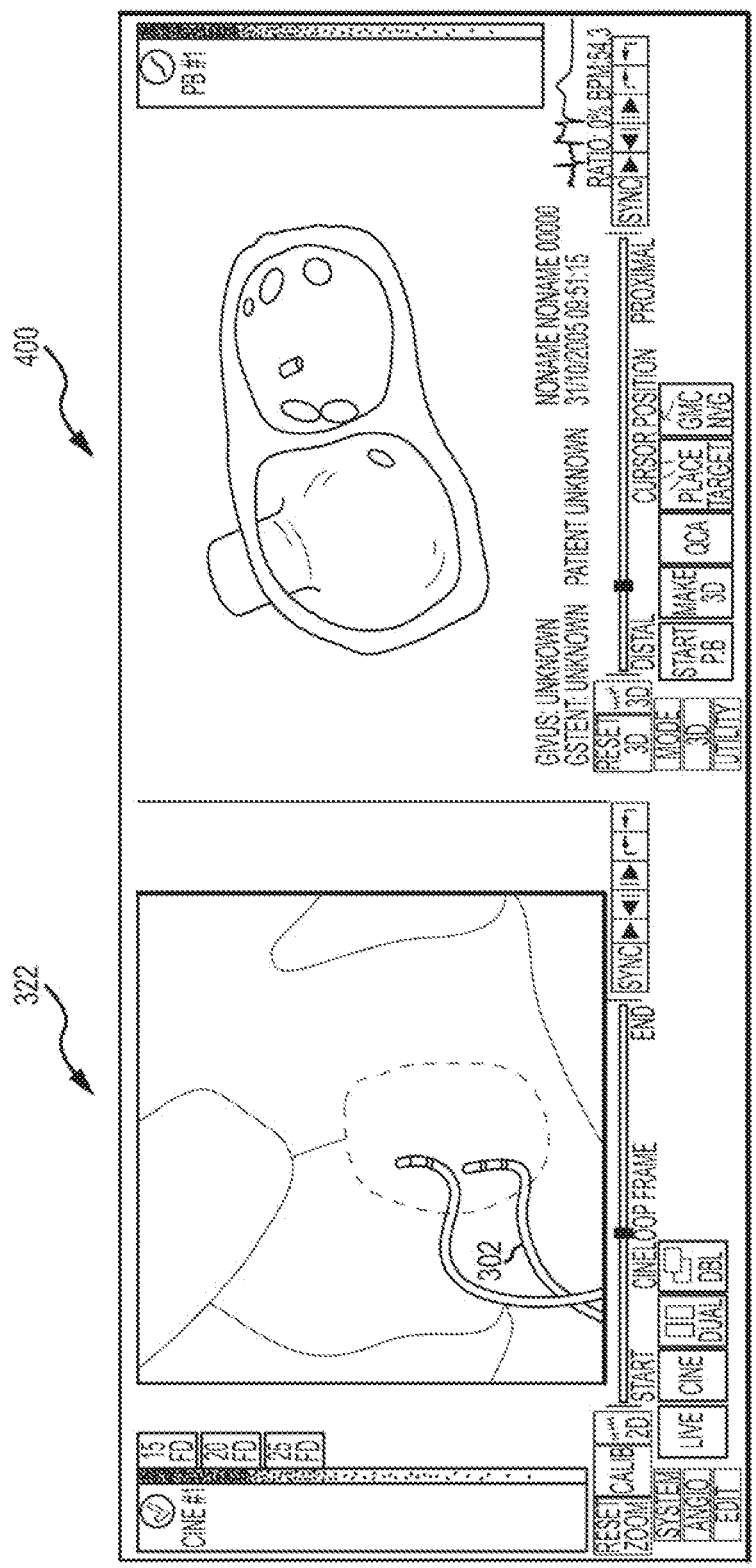
FIG. 4K is a schematic illustration of the GUI of FIG. 4J, during navigation to another point within the heart chamber.
Figure 4L:
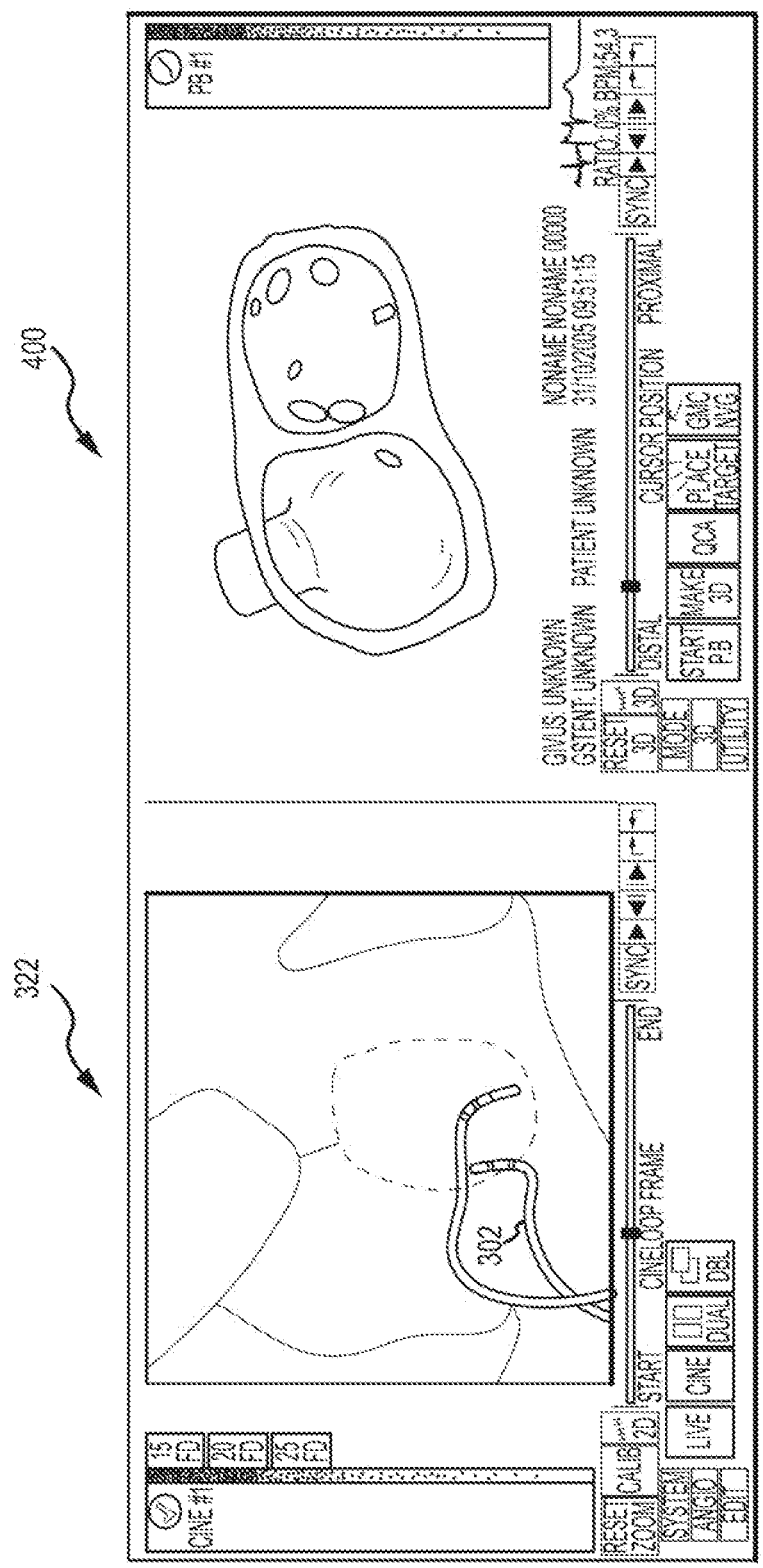
FIG. 4L is a schematic illustration of the GUI of FIG. 4J, during navigation to a further point within the heart chamber.

Reference is now made to FIGS. 4A, 4B, 4C, 4D, 4E, 4F, 4G, 4H, 4J, 4K, and 4L. FIG. 4A is a schematic illustration of a graphical user interface (GUI) including a real time two dimensional image of the heart chamber of the heart of the body of a patient, generally referenced 300, and a previously acquired three-dimensional image of the heart chamber, generally referenced 400, at a stage prior to registration of an MPS with an image detector detecting the two-dimensional image, constructed and operative according to a further embodiment of the disclosed technique. FIG. 4B is a schematic illustration of the GUI of FIG. 4A, during registration of the MPS with the image detector. FIG. 4C is a schematic illustration of the GUI of FIG. 4A, during navigation of a probe catheter within the heart chamber. FIG. 4D is a schematic illustration of the GUI of FIG. 4C, during further navigation of the probe catheter of FIG. 4C, to another known point on the inner heart chamber surface. FIG. 4E is a schematic illustration of the GUI of FIG. 4C, during navigation of the probe of FIG. 4C, to a further known point on the inner heart chamber surface. FIG. 4F is a schematic illustration of the GUI including a two-dimensional real-time image of the heart chamber, and a previously acquired three-dimensional image of the heart chamber, including an electrophysiological map the heart chamber, constructed and operative according to a further embodiment of the disclosed technique. FIG. 4G is a schematic illustration of the GUI of FIG. 4F, during ablation of a region of a pulmonary vein of the heart of the patient. FIG. 4H is a schematic illustration of the GUI of FIG. 4F, during ablation of another region of the pulmonary vein of the heart. FIG. 4J is a schematic illustration of a GUI including a previously acquired two-dimensional image 322 of the heart chamber, and a previously acquired three dimensional image of the heart chamber, constructed and operative according to another embodiment of the disclosed technique, during navigation of the probe catheter to a known point on the inner heart chamber surface. FIG. 4K is a schematic illustration of the GUI of FIG. 4J, during navigation to another known point on the inner heart chamber surface. FIG. 4L is a schematic illustration of the GUI of FIG. 4J, during navigation to a further known point on the inner heart chamber surface.

With reference to FIG. 4A, a 2D image detector (not shown) detects two dimensional real time image 300. A tomographic image detector detects three-dimensional image 400. The tomographic image detector detects three-dimensional image 400 prior to the medical operation on the patient. A probe catheter 302 is inserted into a left atrium 304 of the heart of the patient. Probe catheter 302 is similar to probe catheter 162 as described herein above in connection with FIG. 1B, and includes an MPS sensor (not shown), and a probe 308 at the tip thereof. An MPS (not shown) is coupled with the MPS sensor and with a processor (not shown). A heart parameter measuring unit (not shown) is coupled with probe 308 and with the processor.

With reference to FIG. 4B, the MPS is registered with the tomographic image detector. The MPS is similar to MPS 154 as described herein above in connection with FIG. 1B.

With reference to FIG. 4C, the surgeon navigates probe catheter 302 within atrium 304, to a known point 306, by observing probe 308 in two dimensional real time image 300, and a representation 310 of the position of probe 308 in three-dimensional image 400. The heart parameter measuring unit determines a heart parameter (e.g., electric potential) at point 306, according to an output of probe 308. The MPS determines the position of probe 308 at point 306, according to an output of the MPS sensor. The processor associates this heart parameter with the same position.

With reference to FIGS. 4D and 4E, the surgeon navigates probe catheter 302 to known points 312 and 314, respectively, by observing respective representations 316 and 318 of the position of probe 308, in three-dimensional image 400. The surgeon can also observe probe 308 in two-dimensional real-time image 300. The surgeon continues to navigate probe catheter 302 within the heart chamber, to additional known points sufficient for the processor to construct an electrophysiological map the heart chamber.

For example, the heart parameter measuring unit determines the value of the heart parameter at each of points 306, 312, and 314, according to an output of probe 308, and sends data respective of these values to the processor. The MPS confirms the position of probe 308 at each of known points 306, 312, and 314, according to an output of the MPS sensor, and sends data respective of these positions to the processor. The processor associates the value of the heart parameter at each of known points 306, 312, and 314, with the respective position determined by the MPS, and in this manner constructs an electrophysiological map of the heart chamber (FIG. 4F), based on the electric potential measurements and the 3D inner surface of the cardiac chamber. With reference to FIGS. 4G and 4H, the surgeon ablates different regions of the heart chamber, by employing an ablating catheter 320.

With reference to FIGS. 4J, 4K, and 4L, the surgeon can navigate probe catheter 302 within the heart chamber, similar to the way described herein above in connection with FIGS. 4C, 4D, and 4E, except that the surgeon can observe probe 308 in a previously acquired two-dimensional image 322, instead of two-dimensional real-time image 300. Hence, in case of a fluoroscope, the surgeon and the patient are exposed to a minimal amount of radioactive radiation. The surgeon can still observe the real-time representation of the position of probe 308, in previously acquired three-dimensional image 400. It will be appreciated by persons skilled in the art that the disclosed technique is not limited to what has been particularly shown and described hereinabove. Rather the scope of the disclosed technique is defined only by the claims, which follow.

The invention claimed is:

1. An apparatus, comprising:
a medical positioning system (MPS) comprising circuitry to detect a current position and a current orientation of an MPS sensor coupled to a tip portion of a probe catheter;
a first processor comprising circuitry to electrically communicate with said MPS and with an image detector configured to detect a first image of a heart, said first processor being adapted to register the MPS with the image detector;
a second processor comprising circuitry to determine a respective tissue target location and a respective target probe orientation, at which at least one heart parameter value is to be measured for each of a plurality of tissue targets within said heart;
a third processor comprising circuitry to confirm that said tip portion is located at said respective tissue target location by comparing a currently detected location of said tip portion with said respective tissue target location;
a fourth processor comprising circuitry to confirm that said tip portion is oriented at said respective target probe orientation by comparing a currently detected orientation of said tip portion with said respective target probe orientation;
a heart parameter measurement unit configured to measure said at least one heart parameter value via a heart parameter sensor coupled to said tip portion; and
a fifth processor comprising circuitry to superimpose said at least one heart parameter value at said respective tissue target locations on a second image of said heart to produce an electrophysiological map of said heart.

2. An apparatus according to claim 1, wherein the at least one heart parameter comprises one of: a local activation time (LAT), a respiration artifact, and a change in electrical potential.

3. An apparatus according to claim 1, wherein at least one of the first image of said heart and the electrophysiological map of said heart comprises a two dimensional depiction.

4. An apparatus according to claim 1, wherein at least one of the first image of said heart and the electrophysiological map of said heart comprises a three dimensional depiction.

5. An apparatus according to claim 1, further comprising a sixth processor comprising circuitry to register a plurality of superimposed images.

6. An apparatus according to claim 1, wherein said first, second, third, fourth, and fifth processors comprise a single processor.

7. An apparatus according to claim 1, further comprising a stimulation catheter comprising circuitry to stimulate a portion of the heart.

8. An apparatus according to claim 7, wherein the stimulation catheter comprises one of an elongate temporary pacing lead and an electrophysiology catheter.

9. An apparatus according to claim 8, wherein the pacing lead and the electrophysiology catheter are adapted to couple to a location on or near a coronary sinus structure of the heart.

10. An apparatus according to claim 1, wherein at least a portion of one of the first image of said heart and the electrophysiological map of said heart is generated by one of: an x-ray imaging system, a computed tomography imaging system, a positron emission tomography imaging system, an ultrasound imaging system, an infrared imaging system, a single photon emission computed tomography imaging system, a magnetic resonance imaging system, a magnetically-based position and orientation system, an impedance-based visualization system, and an electrophysiology catheter.

11. An apparatus according to claim 10, wherein the first image of said heart comprises a previously acquired image.

12. An apparatus according to claim 1, further comprising an organ monitor electrically coupled to the heart parameter sensor.

13. An apparatus according to claim 12, wherein said third processor is further configured to produce at least one of an aural and a visual output signifying that the tip portion is located at one of said plurality of tissue targets and/or is oriented in a predetermined orientation.

14. An apparatus according to claim 1,
wherein said heart parameter measurement unit further comprises circuitry coupled to said probe catheter for saving a detected heart parameter in a memory structure.

15. An apparatus according to claim 14, wherein the heart parameter sensor comprises an electrode coupled to circuitry for measuring electrical potential.

16. An apparatus according to claim 14, wherein said image detector is configured to detect said first image of said heart during a procedure.

* * * * *

UNITED STATES PATENT AND TRADEMARK OFFICE
CERTIFICATE OF CORRECTION

| | | |
|---|---|---|
| PATENT NO. | : 8,706,195 B2 | Page 1 of 1 |
| APPLICATION NO. | : 12/599225 | |
| DATED | : April 22, 2014 | |
| INVENTOR(S) | : Gera Strommer et al. | |

It is certified that error appears in the above-identified patent and that said Letters Patent is hereby corrected as shown below:

On the title page of the patent item (75), line 3, where the inventors are listed, please delete "Arnit Cohen" and replace with Amit Cohen.

Signed and Sealed this
Nineteenth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,706,195 B2  Page 1 of 1
APPLICATION NO. : 12/599225
DATED : April 22, 2014
INVENTOR(S) : Strommer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1079 days.

Signed and Sealed this
Twenty-ninth Day of September, 2015

Michelle K. Lee
*Director of the United States Patent and Trademark Office*